(12) United States Patent
Takeguchi et al.

(10) Patent No.: US 10,543,291 B2
(45) Date of Patent: Jan. 28, 2020

(54) CELL FOR ULTRAVIOLET IRRADIATION MODULE AND ULTRAVIOLET IRRADIATION MODULE

(71) Applicant: ASAHI KASEI KABUSHIKI KAISHA, Tokyo (JP)

(72) Inventors: Keigo Takeguchi, Tokyo (JP); Sho Sugiyama, Tokyo (JP); Hiroyuki Kishi, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/331,790

(22) PCT Filed: Jan. 31, 2018

(86) PCT No.: PCT/JP2018/003298
§ 371 (c)(1),
(2) Date: Mar. 8, 2019

(87) PCT Pub. No.: WO2018/143304
PCT Pub. Date: Aug. 9, 2018

(65) Prior Publication Data
US 2019/0358356 A1 Nov. 28, 2019

(30) Foreign Application Priority Data

Jan. 31, 2017 (JP) .................. 2017-015697

(51) Int. Cl.
*A61L 2/26* (2006.01)
*C02F 1/32* (2006.01)
(Continued)

(52) U.S. Cl.
CPC .................. *A61L 2/26* (2013.01); *A61L 2/10* (2013.01); *C02F 1/325* (2013.01); *C08F 14/26* (2013.01);
(Continued)

(58) Field of Classification Search
CPC ........ A61L 2/26; A61L 2/10; A61L 2202/122; A61L 2202/11; G02B 5/0891;
(Continued)

(56) References Cited

U.S. PATENT DOCUMENTS

2004/0195173 A1  10/2004  Huang et al.
2015/0314024 A1*  11/2015  Khan et al. ............... A61L 2/10

FOREIGN PATENT DOCUMENTS

JP  H11-319817 A  11/1999
JP  2004-066045 A  3/2004
(Continued)

OTHER PUBLICATIONS

Ferry, et al ("Study of polytetrafluoroethylene crystallization" Acta Polymer, 46, 300-306 (1995)) (Year: 1995).*
(Continued)

*Primary Examiner* — Michael Maskell
(74) *Attorney, Agent, or Firm* — Morgan, Lewis & Bockius LLP

(57) ABSTRACT

The present invention is intended to provide a cell for an ultraviolet irradiation module and an ultraviolet irradiation module with which it is possible to improve the efficiency of sterilizing an object to be irradiated to a greater extent than in the past. The cell for an ultraviolet irradiation module includes a case being at least partially formed of polytetrafluoroethylene having a crystallite size in a direction of 60 nm or more and 250 nm or less and having an internal space into which an object to be irradiated can be introduced.

20 Claims, 2 Drawing Sheets

(51) Int. Cl.
  *A61L 2/10* (2006.01)
  *C08F 14/26* (2006.01)
  *G02B 5/08* (2006.01)
(52) U.S. Cl.
  CPC ......... *G02B 5/0891* (2013.01); *A61L 2202/11* (2013.01); *A61L 2202/122* (2013.01); *C02F 2201/3222* (2013.01); *C02F 2201/3228* (2013.01)
(58) Field of Classification Search
  CPC .............. C02F 1/325; C02F 2201/3222; C02F 2201/3228; C08F 14/26
  USPC ........................... 250/453.11–455.11, 504 R
  See application file for complete search history.

(56) References Cited

FOREIGN PATENT DOCUMENTS

| | | |
|---|---|---|
| JP | 2013-158722 A | 8/2013 |
| WO | 2014/115146 A1 | 7/2014 |

OTHER PUBLICATIONS

Silva et al., "Reflectance of polytetrafluoroethylene for xenon scintillation light", Journal of Applied Physics, 107, 064902, Mar. 17, 2010.
International Search Report (with partial translation) and Written Opinion dated Mar. 13, 2018, issued in corresponding International Patent Application No. PCT/JP2018/003298.
International Preliminary Report on Patentability for International Application No. PCT/JP2018/003298 dated Aug. 15, 2019, 8 pages.

* cited by examiner

CELL FOR ULTRAVIOLET IRRADIATION MODULE AND ULTRAVIOLET IRRADIATION MODULE

TECHNICAL FIELD

The present invention relates to a cell for an ultraviolet irradiation module and an ultraviolet irradiation module.

BACKGROUND ART

In recent years, an ultraviolet light irradiation method has been widely used to sterilize microorganisms such as filamentous fungi, bacteria, and viruses contained in atmosphere or a liquid such as water. Irradiation with especially C wave (UVC) at a wavelength of 280 nm or less among ultraviolet light is said to cause disruption of a function of DNA replication of viruses and exhibit a really high effect of killing viruses.

For the above-described reasons, a low-pressure mercury lamp which efficiently emits ultraviolet light at 254 nm has been widely used as a light source for sterilization and has been commercialized.

To efficiently use output of the light source, a method in which a low-pressure mercury lamp is placed in a cell for sterilization as a light source and the inside of the cell is coated with a highly reflective material has been proposed (e.g., see PTL 1).

However, the low-pressure mercury lamp has a problem in that the exchange frequency is high because of the short service life as a light source, and it takes time and effort to maintain. Moreover, when the low-pressure mercury lamp is used as a light source, the size of the whole cell including a power unit and the like is increased, and it is difficult to downsize the cell.

Therefore, a method using, as a light source, an ultraviolet LED as a substitute for a low-pressure mercury lamp has been proposed. An LED has a long service life and is small and light, and thus it is easy to downsize the cell (e.g., PTL 2). However, optimization of a material of a cell into which an object to be irradiated (fluid) is introduced to enhance sterilization efficiency in the method using an ultraviolet LED as a light source has not been sufficiently studied yet.

CITATION LIST

Patent Literatures

PTL 1: JP H11-319817 A
PTL 2: JP 2013-158722 A

SUMMARY OF INVENTION

Technical Problem

The present invention is intended to provide a cell for an ultraviolet irradiation module and an ultraviolet irradiation module with which it is possible to improve the efficiency of sterilizing an object to be irradiated.

Solution to Problem

A cell for an ultraviolet irradiation module according to an embodiment of the present invention includes a case being at least partially formed of polytetrafluoroethylene having a crystallite size in a (110) direction of 60 nm or more and 250 nm or less and having an internal space into which an object to be irradiated can be introduced.

An ultraviolet irradiation module according to an embodiment of the present invention includes the cell for an ultraviolet irradiation module according to the embodiment of the present invention and an ultraviolet irradiation device capable of irradiating the internal space of the case with ultraviolet light.

Advantageous Effects of Invention

With the embodiments of the present invention, the efficiency of sterilizing an object to be irradiated can be improved.

DESCRIPTION OF EMBODIMENTS

Figure 1:
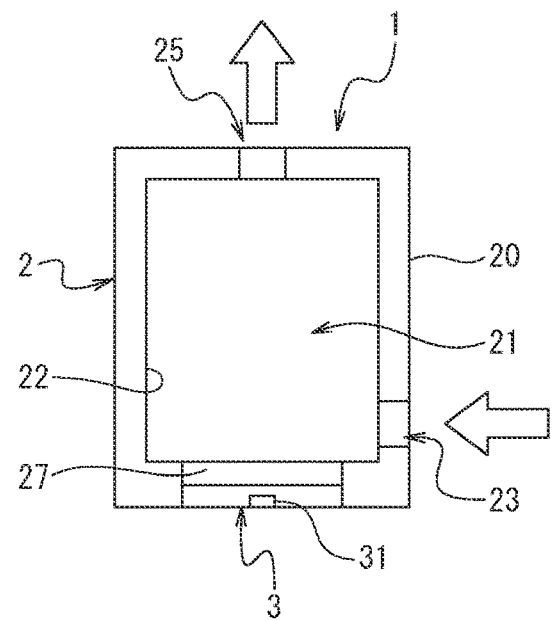
FIG. 1 is a drawing illustrating an example of an ultraviolet irradiation module according to an embodiment of the present invention.

The following describes embodiments (hereinafter referred to as present embodiments) of the present invention with reference to the drawings.

The following detailed description includes many certain specific configurations to provide complete understanding of the embodiments of the present invention. The present invention, however, is by no means limited to such certain specific configurations, and other embodiments can obviously be employed. In addition, the following embodiments do not limit the inventions according to claims. Not all of the combinations of characteristics described in the embodiments are necessary to solve the problem by the present invention.

<Cell for Ultraviolet Irradiation Module>

A cell for an ultraviolet irradiation module according to an embodiment of the present invention includes a case being at least partially formed of polytetrafluoroethylene (PTFE) having an average crystallinity of 0.51 or more and 0.61 or less and a crystallite size in a (110) direction of 60 nm or more and 250 nm or less and having an internal space into which an object to be irradiated can be introduced.

In the cell for an ultraviolet irradiation module according to the embodiment of the present invention, the case is at least partially formed of PTFE having a high reflectance for ultraviolet light. Thus, the amount of ultraviolet light in the internal space of the case, i.e., the density of the ultraviolet light in the internal space of the case can be enhanced, and the efficiency of sterilizing an object to be irradiated can be improved.

<Ultraviolet Irradiation Module>

An ultraviolet irradiation module according to an embodiment of the present invention includes the cell for an ultraviolet irradiation module of the present invention and an ultraviolet irradiation device capable of irradiating an internal space of a case with ultraviolet light.

In the ultraviolet irradiation module according to the present embodiment, the case is at least partially formed of PTFE having a high reflectance for ultraviolet light. The ultraviolet light from the ultraviolet irradiation device can remain in the internal space of the case for a long period of time. In this manner, with the ultraviolet irradiation module according to the present embodiment, the efficiency of sterilizing an object to be irradiated introduced into the internal space of the case can be improved.

The following describes components of the ultraviolet irradiation module according to the present invention in further detail.

<Case>

An object to be irradiated can be introduced into an internal space of a case. Moreover, the case is at least partially formed of PTFE having an average crystallinity of 0.51 or more and 0.61 or less and a crystallite size in a (110) direction of 60 nm or more and 250 nm or less.

Here, at least a part of the case means that the PTFE is used in at least a part of a member for forming the case. As an example, the case may be tubular, and the PTFE may be used in the inner surface of the tube. Alternatively, the inner surface of the tubular case may be formed of an ultraviolet transmitting member, and the outer surface of the tubular case may be formed of the PTFE.

The shape of the case is not limited to tubular and may be any shape as long as the case has an internal space, and an object to be irradiated can be introduced into this internal space of the case. An example of the shape of the case can be cylindrical and is however not particularly limited thereto. The case may include an inlet for introducing an object to be irradiated into the inside and an outlet for leading the object out from the inside to the outside.

To effectively use the ultraviolet light from the light source utilizing the reflectivity of the PTFE, the structure of the case relative to the light source is preferably configured so that 30% or more of a region of the case is composed of PTFE as a relative solid angle when the case is viewed (projected) from the center position of the light source. More preferably, 50% or more of a region of the case is composed of PTFE, most preferably, 70% or more of a region of the case is composed of PTFE. The relative solid angle represents a value of a rate obtained by assuming steregon as denominator and a solid angle at which PTFE is projected as numerator in terms of percentage. When the region of the case composed of PTFE is 30% or more, multiple reflection can substantially be utilized by PTFE which is a diffuse-reflective substance. When the region of the case composed of PTFE is 50% or more, an effect of effectively utilizing ultraviolet light by multiple reflection is enhanced. When the region of the case composed of PTFE is 70% or more, at least half of incident light is multiply reflected at least twice, and the effect of effectively utilizing ultraviolet light is really enhanced. The upper limit is desirably 100%. However, the upper limit is limited by practical components such as an energy supply route to the light source and the inlet of the fluid. Thus, 100% of the region of the case is practically difficult to be composed of the PTFE in an actual module.

In the cell for an ultraviolet irradiation module according to an embodiment of the present invention, 30% or more and 99% or less (an example of at least a portion of the case) of the surface area of the inside of the case as a relative solid angle when the case is projected from the center position of the light source is required to be composed of polytetrafluoroethylene (PTFE) satisfying at least one of the condition where the crystallite size in a (110) direction is 60 nm or more and 250 nm or less or the condition where the average crystallinity is 0.51 or more and 0.61 or less.

To efficiently cause multiple reflection of ultraviolet light from the light source utilizing diffuse-reflectivity of the PTFE and effectively use energy of radiation, the structure of the case for effectively utilizing light radiation in the internal space is preferably configured so that 30% or more of the region of the case is composed of the PTFE as a relative solid angle when the case is viewed from the center position of the internal space. More preferably, 50% or more of a region of the case is composed of PTFE, most preferably, 70% or more of a region of the case is composed of PTFE. The upper limit is desirably 100%. However, the upper limit is limited by practical components such as an energy supply route to the light source and the inlet of the fluid. Thus, 100% of the region of the case is practically difficult to be composed of the PTFE in an actual module.

30% or more and 99% or less (an example of at least a portion of the case) of the surface area of the inside of the case as a relative solid angle when the case is projected from the center position of the internal space is required to be composed of polytetrafluoroethylene (PTFE) satisfying at least one of the condition where the crystallite size in a (110) direction is 60 nm or more and 250 nm or less or the condition where the average crystallinity is 0.51 or more and 0.61 or less.

To more efficiently receive ultraviolet light from the light source in a process of flowing an object to be irradiated, the structure of the case for effectively irradiating the object to be irradiated with light is preferably configured so that 30% or more of the region of the case as a relative solid angle when the case is viewed from the midpoint of a straight light connecting between the inlet and the outlet is composed of the PTFE. More preferably, 50% or more of a region of the case is composed of PTFE, most preferably, 70% or more of a region of the case is composed of PTFE. The upper limit is desirably 100%. However, the upper limit is limited by practical components such as an energy supply route to the light source and the inlet of the fluid. Thus, 100% of the region of the case is practically difficult to be composed of the PTFE in an actual module.

30% or more and 99% or less (an example of at least a portion of the case) of the surface area of the inside of the case as a relative solid angle when the case is projected from the midpoint of a straight line connecting between the inlet and the outlet is required to be composed of polytetrafluoroethylene (PTFE) satisfying at least one of the condition where the crystallite size in a (110) direction is 60 nm or more and 250 nm or less or the condition where the average crystallinity is 0.51 or more and 0.61 or less.

(Method for Measuring Average Crystallinity)

The average crystallinity (X) and the crystallite size (D) of PTFE to be used in the case can be measured as follows.

The average crystallinity (X) and the crystallite size (D) are obtained from the following formulae (1) and (2) based on the measurement results of small angle X-ray scattering and wide angle X-ray scattering (SAXS & WAXS (XRD)).

Device: NANO-Viewer manufactured by Rigaku Corporation

X-ray wavelength λ: 0.154 nm

Optical system: point collimation

1st slit: φ0.4 mm

2nd slit: φ0.2 mm

Guard slit: φ0.8 mm

Measurement time: 900 seconds

Detector: (SAXS) PILATUS 100K, (WAXS) imaging plate

Camera length: (SAXS) 841 mm, (WAXS) 75.3 mm

Sample: the PTFE to be used in the case, cut into a thickness: about 0.5 mm was subjected to measurement

[Math. 1]
$$X = \frac{\sum A_{ci}}{A_a + \sum A_{ci}} \quad (1)$$

Aa: amorphous peak area, Ac: crystal peak area

[Math. 2]
$$D = \frac{K\lambda}{\sqrt{\beta^2 - b^2} \cos\theta} \quad (2)$$

K: Scherrer constant (constant depending on the shape and the like of crystallite)
β: half width of peak (full width at half maximum: FWHM) (rad)
b: half width of spread of incident beam (full width at half maximum: FWHM) (rad)

The density of PTFE may be 2160 kg/m³ or more and 2180 kg/m³ or less.

(Method for Measuring Density)

The density of PTFE to be used in the case can be measured by an A method (underwater substitution) in accordance with JIS K 7112, and a test piece has a size of 18×18×2 mm thickness.

At least a part of the inner surface of the case may have a reflectance of 94% or more for ultraviolet light at a wavelength of 265 nm. With the reflectance, the amount of ultraviolet light (density) inside the internal space of the case can be increased, and an efficiency of sterilizing an object to be irradiated can be improved.

(Method for Measuring Reflectance)

The ultraviolet reflectance in the internal space of the case can be measured by the ultraviolet-visible spectroscopy (UV-Vis). In the present embodiment, the reflectance was measured by the ultraviolet-visible spectroscopy using UV-2450 manufactured by Shimadzu Corporation, for example. The test piece has a size of φ50×2 mm thickness.

<Ultraviolet Irradiation Device>

The ultraviolet irradiation device of the ultraviolet irradiation module according to an embodiment of the present invention is not particularly limited as long as the internal space of the case can be irradiated with ultraviolet light. As the ultraviolet irradiation device, a device or element capable of performing irradiation with ultraviolet light such as an ultraviolet lamp and an ultraviolet LED can be used. The wavelength of ultraviolet light is not particularly limited as long as it is 10 nm or more and 400 nm or less, and from the viewpoint of efficiency of sterilizing bacteria and the like, the peak wavelength may be 200 nm or more and 300 nm or less. As an ultraviolet irradiation device with a peak wavelength of 200 nm or more and 300 nm or less, a device using a nitride semiconductor layer (e.g., AlN, AlGaN, AlGaInN) as a light emission layer is preferable. The ultraviolet irradiation device produces heat, and the ultraviolet irradiation device is thus required to include a heat radiation mechanism if necessary. The heat radiation mechanism can be, although not limited to, a mechanism or the like using an air-cooling system or a water-cooling system. As the heat radiation mechanism, a heat radiation fin or an air-cooling fan using an aluminium plate having a high thermal conductivity can be used, for example.

The object to be irradiated in the present invention has fluidity and indicates, for example, a liquid such as water, an aqueous solution, and an emulsion or a powder composed of many fine grains or particles such as ice and sand. The liquid means all of liquid having fluidity such as water, an aqueous solution, and an emulsion and can be a potable liquid or non-potable liquid.

Examples of the potable liquid include water, soft drinks, dairy drinks, milk, and edible oils. Examples of the potable liquid further include sherbert, jelly, soft ice cream, smoothy, and cocoa/chocolate drinks.

Examples of non-potable liquid include ultrapure water, cleaning water, mildly acidic water, and mildly alkaline water or industrial products such as aqueous industrial material solutions and water-based paints.

As described above, the object to be irradiated in the present invention has fluidity and is, for example, a liquid or a powder.

Specific Examples of Embodiment

The following describes specific examples of the cell for an ultraviolet irradiation module and the ultraviolet irradiation module according to the present embodiments with reference to the drawings.

FIG. 1 is a drawing illustrating an example of an ultraviolet irradiation module and a cell for an ultraviolet irradiation module according to the present embodiments.

The ultraviolet irradiation module 1 according to the present embodiment includes a cell 2 for an ultraviolet irradiation module and an ultraviolet irradiation device 3. The cell 2 for an ultraviolet irradiation module includes a case 20. In FIG. 1, the shape of the case 20 is tubular and is however not particularly limited to this shape. The case 20 includes an internal space 21 in which an object to be irradiated is stored, an inner surface 22 which partially reflects ultraviolet light entering the internal space 21 toward the internal space 21 of the case 20, an inlet 23 configured to introduce an object to be irradiated to the internal space 21, and an outlet 25 configured to lead-out the object to be irradiated from the internal space 21. As illustrated in FIG. 1, the case 20 includes a quartz window 27 formed from a quartz plate at the bottom surface.

The ultraviolet irradiation device 3 includes a light-emitting diode capable of performing ultraviolet irradiation (e.g., UVC-LED) as a light source 31. The ultraviolet light from the ultraviolet irradiation device 3 enters the internal space 21 of the case 20 via the quartz window 27 and sterilizes an object to be irradiated introduced into the internal space 21. The case 20 is at least partially formed of PTFE having an average crystallinity of 0.51 or more and 0.61 or less and a crystallite size in a (110) direction of 60 nm or more and 250 nm or less. In this manner, the cell 2 for an ultraviolet irradiation module can partially reflect ultraviolet light entering the internal space 21 from the ultraviolet irradiation device 3 toward the internal space 21 at the inner surface 22 of the case 20. Thus, the ultraviolet irradiation module 1 including the cell 2 for an ultraviolet irradiation module can enhance the amount of ultraviolet light in the internal space 21 of the case 20, i.e., the density of ultraviolet light in the internal space 21. In this manner, with the ultraviolet irradiation module 1 according to the present embodiment, the efficiency of sterilizing an object to be irradiated introduced into the case 20 can be improved.

EXAMPLES

The following describes examples of the cell for an ultraviolet irradiation module and the ultraviolet irradiation module according to the present embodiment.

Example 1

Average crystallinity: 0.54, Crystallite size in (110) direction: 110 nm

Figure 2:
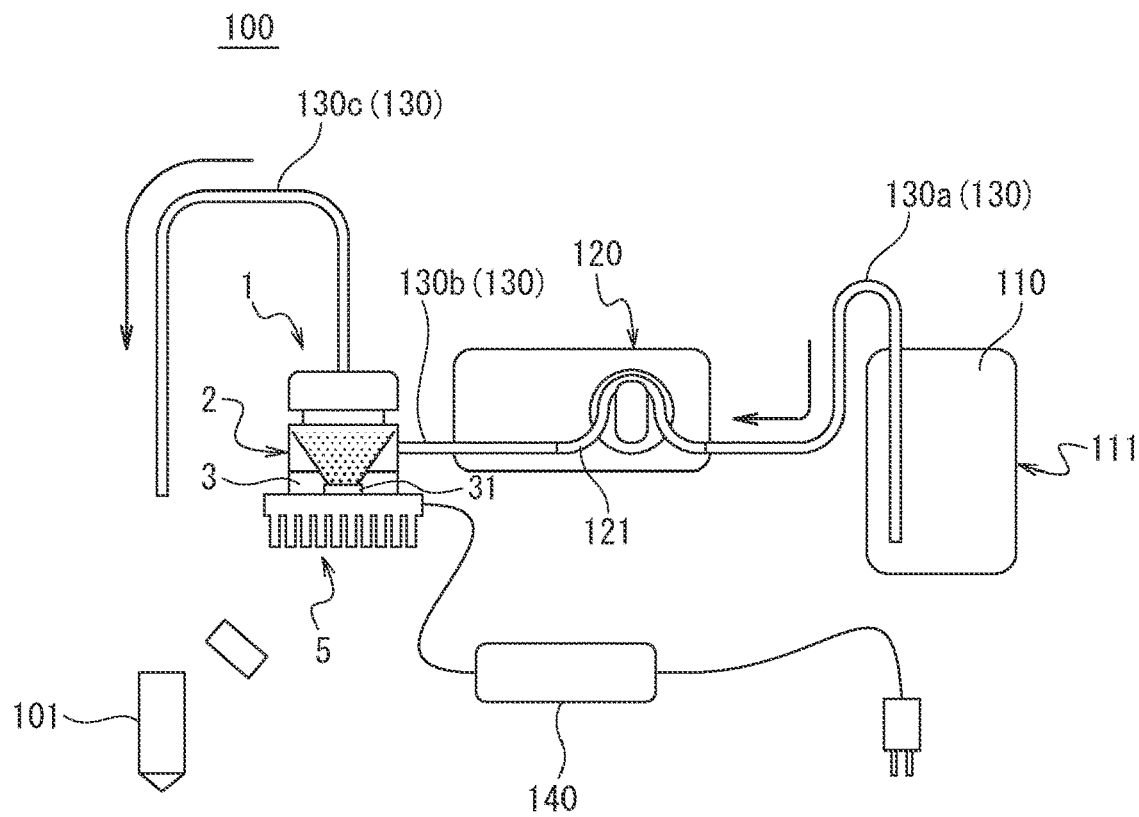
FIG. 2 is a drawing illustrating an example of an ultraviolet sterilization device using the ultraviolet irradiation module according to the embodiment of the present invention.

As illustrated in FIG. 2, in the present example, an object to be irradiated was subjected to a sterilization treatment using an ultraviolet sterilization device 100 including an ultraviolet irradiation module 1 according to the present embodiment, and a bacterial count of the object to be irradiated after the sterilization treatment was measured. As illustrated in FIG. 2, the ultraviolet sterilization device 100 includes a bacterial liquid 110, a tubing pump 120 (WM-520U manufactured by ISOWATEC Corporation), the ultraviolet irradiation module 1, silicon tubes 130 (inner diameter/outer diameter: φ6/φ10 (mm)), and a driver 140.

In the ultraviolet sterilization device 100, a container 111 filled with the bacterial liquid 110, the tubing pump 120, and the ultraviolet irradiation module 1 are connected via the silicon tubes 130. A silicon tube 130a on the side of the container 111 into which the bacterial liquid 110 has been introduced and a silicon tube 130b on the side of the ultraviolet irradiation module 1 are connected via a vinyl chloride tube 121 (inner diameter/outer diameter: φ8/φ12 (mm)) in a liquid sending potion of the tubing pump 120. In this manner, the bacterial liquid 110 is introduced into an internal space 21 (see FIG. 1) of a case 20 configuring the cell 2 for an ultraviolet irradiation module via the silicon tubes 130 (130a, 130b).

As an electrical driving source, the driver 140 is connected to an ultraviolet irradiation device 3 of the ultraviolet irradiation module 1. The driver 140 is connected to a power supply device (not shown), and power is supplied to the ultraviolet irradiation device 3 via the driver 140. The ultraviolet irradiation module 1 further includes, as a heat radiation mechanism, a heat radiation fin 5 on the lower part.

The bacterial liquid 110 was prepared by diluting *Escherichia coli* (ATCC 8739) with a bacterial count per 1 ml of $10^8$ (cfu/ml) using purified water to have $1.5 \times 10^4$ (cfu/ml).

The case 20 of the cell 2 for an ultraviolet irradiation module was tubular with an inner capacity of about 80 cc, formed by cutting PTFE. A quartz window 27 (see FIG. 1) on the bottom surface of the case 20 is a quartz plate (00 mm), and a bacterial liquid 110 introduced into the ultraviolet irradiation module 1 (in the internal space 21 of the case 20) via the quartz window 27 was irradiated with ultraviolet light using a light source 31 (e.g., UVC-LED) included in the ultraviolet irradiation device 3.

The output of the light source 31 (UVC-LED) included in the ultraviolet irradiation device 3 was adjusted by output current of a direct current source.

The flow rate of the bacterial liquid 110 in the silicon tubes 130 was adjusted to 500 ml/min by the number of revolutions of the tubing pump 120. A bacterial liquid 110 before the sterilization treatment was introduced from the lower part on the side surface of the ultraviolet irradiation module 1 (e.g., an inlet 23 shown in FIG. 1) to the internal space 21 of the case 20 via the silicon tube 130b. A bacterial liquid 110 after the sterilization treatment performed by ultraviolet irradiation with the ultraviolet irradiation device 3 was discharged from the upper surface of the cell 2 for an ultraviolet irradiation module (e.g., an outlet 25 shown in FIG. 1) via the silicon tube 130c.

The bacterial liquid 110 subjected to the sterilization treatment in the ultraviolet sterilization device 100 and discharged via the silicon tube 130c was collected in a 100 cc-capacity spitz tube 101 (e.g., 100 cc-capacity centrifuge tube) shown in FIG. 2. The bacterial liquid 110 collected after the sterilization treatment was spread on an agar medium using a bacteria spreader, the agar medium was then cultured for 24 hours under an environment at a temperature of 37° C. in an incubator, and colonies generated on the agar medium were thereafter counted to measure a bacterial count.

Example 2

Average crystallinity: 0.61, Crystallite size in (110) direction: 110 nm

In Example 2, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity of PTFE which forms a case 20 of the ultraviolet irradiation module 1 in Example 2 was different from that in Example 1 as mentioned above.

Example 3

Average crystallinity: 0.61, Crystallite size in (110) direction: 250 nm

In Example 3, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity and the crystallite size in the (110) direction of PTFE which forms a case 20 of the ultraviolet irradiation module 1 in Example 3 were different from those in Example 1 as mentioned above.

Example 4

Average crystallinity: 0.54, Crystallite size in (110) direction: 60 nm

In Example 4, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the crystallite size in the (110) direction of PTFE which forms a case 20 of the ultraviolet irradiation module 1 in Example 4 was different from that in Example 1 as mentioned above.

Example 5

Average crystallinity: 0.51, Crystallite size in (110) direction: 250 nm

In Example 5, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity and the crystallite size in the (110) direction of PTFE which forms a case 20 of the ultraviolet irradiation module 1 in Example 5 were different from those in Example 1 as mentioned above.

Comparative Example 1

Average crystallinity: 0.54, Crystallite size in (110) direction: 55 nm

In Comparative Example 1, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the crystallite size in the (110) direction of PTFE which forms a case 20 of the ultraviolet irradiation module 1 in Comparative Example 1 was different from that in Example 1 as mentioned above.

Comparative Example 2

Average crystallinity: 0.51, Crystallite size in (110) direction: 260 nm

In Comparative Example 2, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity and the crystallite size in the (110) direction of PTFE which forms a case 20 of the ultraviolet irradiation module 1 in Comparative Example 2 were different from those in Example 1 as mentioned above.

Comparative Example 3

Average crystallinity: 0.50, Crystallite size in (110) direction: 250 nm

In Comparative Example 3, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity and the crystallite size in the (110) direction of PTFE which forms a case 20 of the ultraviolet irradiation module 1 in Comparative Example 3 were different from those in Example 1 as mentioned above.

Comparative Example 4

Average crystallinity: 0.62, Crystallite size in (110) direction: 110 nm

In Comparative Example 4, a bacterial liquid 110 was subjected to a sterilization treatment using the ultraviolet sterilization device 100 illustrated in FIG. 2 in the same manner as in Example 1, and a bacterial count in the bacterial liquid 110 after the sterilization treatment was measured in the same manner as in Example 1. Please note that the average crystallinity of PTFE which forms a case 20 of the ultraviolet irradiation module 1 in Comparative Example 4 was different from that in Example 1 as mentioned above.

<Evaluation Results>

Table 1 below shows sterilization results of bacterial liquids 110 using the ultraviolet sterilization device 100 including the ultraviolet irradiation module 1 illustrated in FIG. 2. Table 1 is roughly divided into two items of "bacterial count" and "survival rate". "Bacterial count" represents a bacterial count (unit: cfu/ml) obtained from 1 ml of each bacterial liquid 110 after the sterilization treatment using the ultraviolet sterilization device 100. "Survival rate" represents a rate (unit: Log (N/N0)) of surviving bacteria after the sterilization treatment using the ultraviolet sterilization device 100 among bacteria (*Escherichia coli* in the present examples) living in each bacterial liquid 110 before the sterilization treatment. N represents the bacterial count per 1 ml of each bacterial liquid 110 after the sterilization treatment, and N0 represents the bacterial count before the sterilization treatment, i.e., $1.5 \times 10^4$ (cfu/ml). Each of the two items of "bacterial count" and "survival rate" is classified into three (10 mW, 15 mW, and 20 mW) by the output of the light source 31 (UVC-LED) included in the ultraviolet irradiation device 3 of the ultraviolet irradiation module 1.

TABLE 1

| | Bacterial count (cfu/ml) | | | Survival rate Log (N/N0) | | |
|---|---|---|---|---|---|---|
| LED output | 10 mW | 15 mW | 20 mW | 10 mW | 15 mW | 20 mW |
| Ex. 1 | 480 | 175 | 99 | −1.49 | −1.93 | −2.18 |
| Ex. 2 | 470 | 160 | 88 | −1.50 | −1.97 | −2.23 |
| Ex. 3 | 490 | 180 | 95 | −1.49 | −1.92 | −2.19 |
| Ex. 4 | 485 | 166 | 85 | −1.49 | −1.96 | −2.24 |
| Ex. 5 | 483 | 170 | 80 | −1.49 | −1.95 | −2.27 |
| Comp. Ex. 1 | 583 | 238 | 131 | −1.41 | −1.80 | −2.06 |
| Comp. Ex. 2 | 595 | 232 | 135 | −1.40 | −1.81 | −2.04 |
| Comp. Ex. 3 | 587 | 240 | 138 | −1.41 | −1.79 | −2.03 |
| Comp. Ex. 4 | 590 | 220 | 140 | −1.41 | −1.83 | −2.02 |

Figure 3:
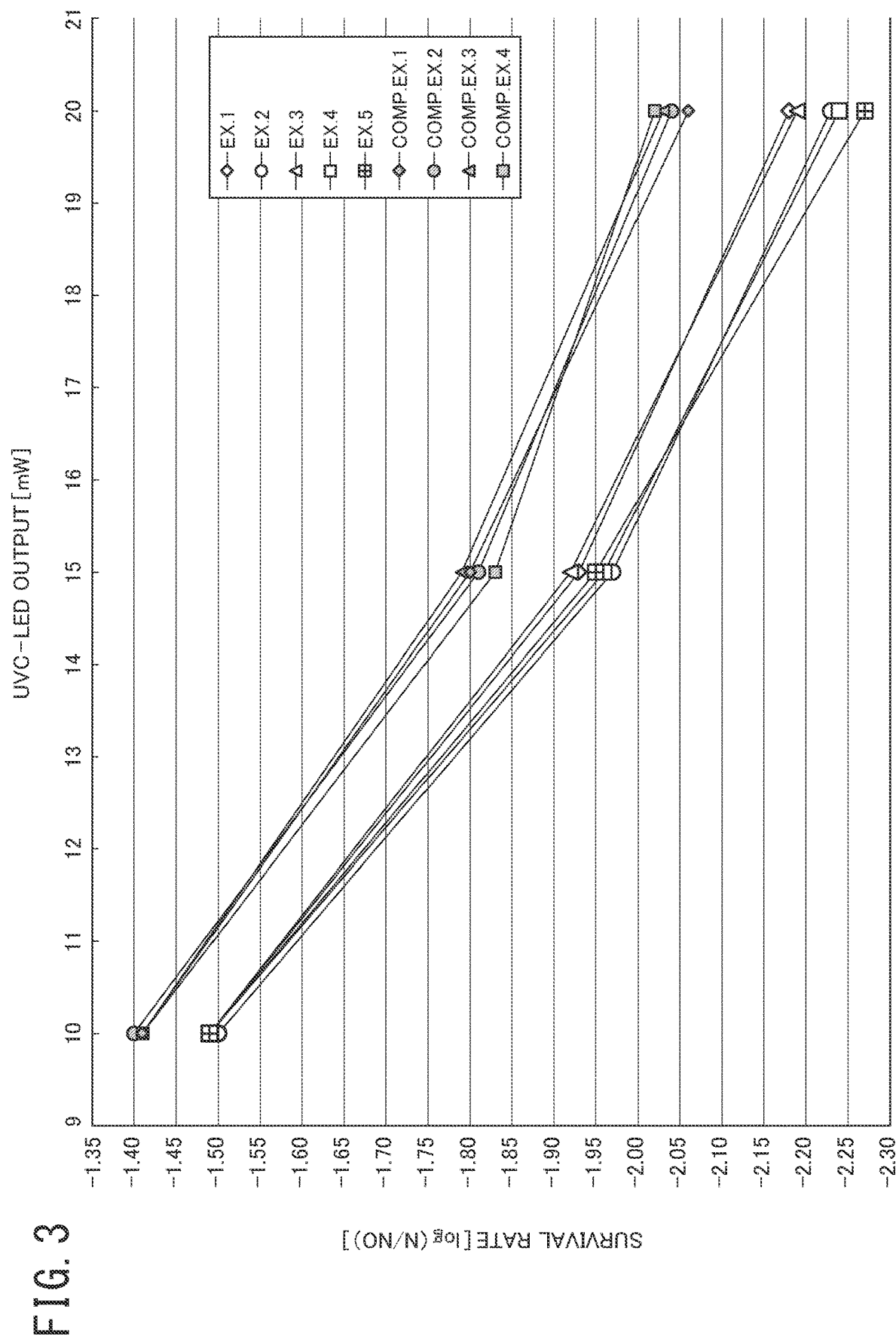
FIG. 3 is a graph illustrating survival rates of bacteria in bacterial liquids after a sterilization treatment using the ultraviolet sterilization device illustrated in FIG. 2.

FIG. 3 is a graph showing the change in survival rate of bacteria in each of the bacterial liquids 110 of Examples 1 to 5 and Comparative Examples 1 to 4 by the output of the LED included in the ultraviolet irradiation device 3. In the graph of FIG. 3, the horizontal axis indicates the output of the light source 31 (UVC-LED) of the ultraviolet irradiation device 3, and the vertical axis indicates the survival rate (unit: Log(N/N0)) of bacteria.

As shown in Table 1, the bacterial counts after the sterilization treatment in all of the cases of the outputs: 10 mW, 15 mW, and 20 mW of the light source 31 (UVC-LED) included in the ultraviolet irradiation device 3 of the ultraviolet irradiation module 1 in Examples 1 to 5 were smaller than those in Comparative Examples 1 to 4. Moreover, as shown in Table 1 and FIG. 3, the survival rate of bacteria after the sterilization treatment in all of the cases of the outputs: 10 mW, 15 mW, and 20 mW of the light source 31 (UVC-LED) included in the ultraviolet irradiation device 3 of the ultraviolet irradiation module 1 in Examples 1 to 5 were smaller than those in Comparative Examples 1 to 4.

As described above, with the ultraviolet irradiation module land the cell 2 for an ultraviolet irradiation module according to the present embodiments, the amount of ultraviolet light in the internal space 21 of the case 20 can be enhanced. Thus, the efficiency of sterilizing the object to be irradiated can be improved.

REFERENCE SIGNS LIST 1 ultraviolet irradiation module
2 cell for an ultraviolet irradiation module 3 ultraviolet irradiation device
31 light source
5 heat radiation fin
20 case
21 internal space
22 inner surface
23 inlet
25 outlet
27 quartz window
100 ultraviolet sterilization device
101 spitz tube
110 bacterial liquid
111 container
120 tubing pump
130, 130a, 130b, 130c silicon tube
140 driver

The invention claimed is:

1. A cell for an ultraviolet irradiation module, comprising:
a case being at least partially formed of polytetrafluoroethylene having a crystallite size in a (110) direction of 60 nm or more and 250 nm or less and comprising an internal space into which an object to be irradiated can be introduced.

2. The cell according to claim 1, wherein the polytetrafluoroethylene has an average crystallinity of 0.51 or more and 0.61 or less.

3. The cell according to claim 1, wherein the polytetrafluoroethylene has a density of 2160 kg/m³ or more and 2180 kg/m³ or less.

4. The cell according to claim 1, wherein an inner surface of the case at least partially has a reflectance of 94% or more for ultraviolet light at a wavelength of 265 nm.

5. The cell according to claim 1, wherein,
30% or more and 99% or less of the surface area of an inside of the case as a relative solid angle when the case is projected from the center position of a light source is composed of the polytetrafluoroethylene satisfying at least one of a condition where the crystallite size in the (110) direction is 60 nm or more and 250 nm or less or a condition where the average crystallinity is 0.51 or more and 0.61 or less.

6. The cell according to claim 1, wherein,
30% or more and 99% or less of the surface area of an inside of the case as a relative solid angle when the case is projected from the center position of the internal space is composed of the polytetrafluoroethylene satisfying at least one of a condition where the crystallite size in the (110) direction is 60 nm or more and 250 nm or less or a condition where the average crystallinity is 0.51 or more and 0.61 or less.

7. The cell according to claim 1, wherein,
30% or more and 99% or less of the surface area of an inside of the case as a relative solid angle when the case is projected from the midpoint of a straight line connecting between an inlet and an outlet is composed of the polytetrafluoroethylene satisfying at least one of a condition where the crystallite size in the (110) direction is 60 nm or more and 250 nm or less or a condition where the average crystallinity is 0.51 or more and 0.61 or less.

8. An ultraviolet irradiation module comprising:
the cell according to claim 1; and
an ultraviolet irradiation device capable of irradiating the internal space of the case with ultraviolet light.

9. The ultraviolet irradiation module according to claim 8, wherein
a light source of the ultraviolet irradiation device is an LED, and
the LED has an emission wavelength of 10 nm or more and 400 nm or less.

10. The ultraviolet irradiation module according to claim 8, wherein the object to be irradiated has fluidity and is a liquid or a powder.

11. The cell according to claim 2, wherein the polytetrafluoroethylene has a density of 2160 kg/m³ or more and 2180 kg/m³ or less.

12. The cell according to claim 2, wherein an inner surface of the case at least partially has a reflectance of 94% or more for ultraviolet light at a wavelength of 265 nm.

13. The cell according to claim 3, wherein an inner surface of the case at least partially has a reflectance of 94% or more for ultraviolet light at a wavelength of 265 nm.

14. The cell according to claim 2, wherein,
30% or more and 99% or less of the surface area of an inside of the case as a relative solid angle when the case is projected from the center position of a light source is composed of the polytetrafluoroethylene satisfying at least one of a condition where the crystallite size in the (110) direction is 60 nm or more and 250 nm or less or a condition where the average crystallinity is 0.51 or more and 0.61 or less.

15. The cell according to claim 3, wherein,
30% or more and 99% or less of the surface area of an inside of the case as a relative solid angle when the case is projected from the center position of a light source is composed of the polytetrafluoroethylene satisfying at least one of a condition where the crystallite size in the (110) direction is 60 nm or more and 250 nm or less or a condition where the average crystallinity is 0.51 or more and 0.61 or less.

16. The cell according to claim 4, wherein,
30% or more and 99% or less of the surface area of an inside of the case as a relative solid angle when the case is projected from the center position of a light source is composed of the polytetrafluoroethylene satisfying at least one of a condition where the crystallite size in the (110) direction is 60 nm or more and 250 nm or less or a condition where the average crystallinity is 0.51 or more and 0.61 or less.

17. The cell according to claim 2, wherein,
30% or more and 99% or less of the surface area of an inside of the case as a relative solid angle when the case is projected from the center position of the internal space is composed of the polytetrafluoroethylene satisfying at least one of a condition where the crystallite size in the (110) direction is 60 nm or more and 250 nm or less or a condition where the average crystallinity is 0.51 or more and 0.61 or less.

18. The cell according to claim 3, wherein,
30% or more and 99% or less of the surface area of an inside of the case as a relative solid angle when the case is projected from the center position of the internal space is composed of the polytetrafluoroethylene satisfying at least one of a condition where the crystallite size in the (110) direction is 60 nm or more and 250 nm or less or a condition where the average crystallinity is 0.51 or more and 0.61 or less.

19. The cell according to claim 4, wherein,
30% or more and 99% or less of the surface area of an inside of the case as a relative solid angle when the case is projected from the center position of the internal space is composed of the polytetrafluoroethylene satisfying at least one of a condition where the crystallite size in the (110) direction is 60 nm or more and 250 nm or less or a condition where the average crystallinity is 0.51 or more and 0.61 or less.

20. The cell according to claim 1, wherein,
30% or more and 99% or less of the surface area of an inside of the case as a relative solid angle when the case is projected from the center position of the internal space is composed of the polytetrafluoroethylene satisfying at least one of a condition where the crystallite size in the (110) direction is 60 nm or more and 250 nm or less or a condition where the average crystallinity is 0.51 or more and 0.61 or less.

* * * * *